United States Patent [19]

Bowman

[11] Patent Number: 4,957,931
[45] Date of Patent: Sep. 18, 1990

[54] CERTAIN 1,2-BENZISOXAZOLE AND 1,2-BENZISOTHIAZOLE DERIVATIVES

[75] Inventor: Robert M. Bowman, Summit, N.J.

[73] Assignee: Ciba-Geigy Corporation, Ardsley, N.Y.

[21] Appl. No.: 367,573

[22] Filed: Jun. 9, 1989

Related U.S. Application Data

[62] Division of Ser. No. 71,124, Jul. 8, 1987, Pat. No. 4,859,691.

[51] Int. Cl.⁵ .................. A61K 31/425; C07D 117/06
[52] U.S. Cl. ...................................... 514/373; 548/207
[58] Field of Search .......................... 548/207; 514/373

[56] References Cited

U.S. PATENT DOCUMENTS

| | | | |
|---|---|---|---|
| 4,150,153 | 4/1979 | Walker | 514/399 |
| 4,172,896 | 10/1979 | Uno et al. | 514/375 |
| 4,206,217 | 6/1980 | Hagen et al. | 514/373 |
| 4,275,071 | 6/1981 | Nordi et al. | 514/396 |
| 4,598,152 | 7/1986 | Davis et al. | 546/198 |
| 4,644,064 | 2/1987 | Shutske | 548/241 |
| 4,723,021 | 2/1988 | Shiokawa et al. | 514/252 |
| 4,742,060 | 5/1988 | Georgiev et al. | 548/240 |
| 4,851,424 | 7/1989 | Allgeier | 514/400 |
| 4,859,691 | 8/1989 | Bowman | 514/379 |

FOREIGN PATENT DOCUMENTS 2313256  3/1972  Fed. Rep. of Germany .

OTHER PUBLICATIONS

K. Clarke et al., J. Chem. Research (S), 1979, 395:als (M) 4677–4692.
H. Hettler, Chemical Abstracts, 65, 16956d, (1966).
K. Walker et al., J. Med. Chem., 24, 67, (1981).
Uno Hitoshi et al., J. Med. Chem., 22, 180, (1979).
D. Nardi et al., J. Med. Chem., 24, 727, (1981).
M. Giannella et al., Chimie Therapeutique, 1972, 127.
Uno Hitoshi et al., Chem. Pharm. Bull., 24, 632, (1976).
Drugs of the Future, 10, 731, (1985).
D. Robertson et al., J. Med. Chem., 30, 939, (1987).
M. Giannella et al., Phytochemistry, 10, 539, (1971).

*Primary Examiner*—Mukund J. Shah
*Assistant Examiner*—C. L. Cseh
*Attorney, Agent, or Firm*—Norbert Gruenfeld

[57] ABSTRACT

Disclosed are 1,2-benzisoxazole and 1,2-benzisothiazole derivatives represented by formula I

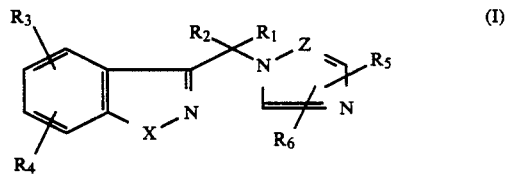

wherein X represents oxygen or sulfur; Z represents carbon (CH) so as to complete the imidazol-1-yl ring radical or Z represents nitrogen (N) so as to complete the 1,2,4-triazol-1-yl ring radical; $R_1$ represents hydrogen, lower alkenyl, lower alkynyl, aryl-lower alkyl or lower alkyl; $R_2$ represents hydrogen, lower alkenyl, lower alkynyl, aryl-lower alkyl or lower alkyl; or $R_1$ and $R_2$ combined represent lower alkylene; or $R_1$ combined with $R_5$ located on the Z-carbon atom of the imidazolyl radical represents $C_2$–$C_4$-alkylene; $R_3$ and $R_4$ independently represent hydrogen, lower alkyl, cycloalkyl, halogen, trifluoromethyl, cyano, nitro, amino, hydroxy, lower alkanoyloxy, carbocyclic aroyloxy, lower alkoxy, or carbocyclic aryl; or $R_3$ and $R_4$, together when located on adjacent carbon atoms, represent lower alkylenedioxy; or $R_3$ and $R_4$, together when located on the carbon atoms to which attached a benzo-fused or $C_5$–$C_7$-cycloalka-fused ring, respectively; $R_5$ located on carbon represents hydrogen, lower alkyl or hydroxy-lower alkyl; $R_6$ located on carbon represents hydrogen or lower alkyl; or when Z represents carbon, $R_5$ located on the Z-carbon atom combined with $R_6$ located on the adjacent carbon atom represents $C_3$–$C_5$-alkylene; and pharmaceutically acceptable salts thereof; which are active in mammals as anticonvulsant agents.

16 Claims, No Drawings

CERTAIN 1,2-BENZISOXAZOLE AND 1,2-BENZISOTHIAZOLE DERIVATIVES

This is a divisional of application Ser. No. 071,124, filed on July 8, 1987.

SUMMARY OF THE INVENTION

The present invention is concerned with 1,2-benzisoxazole and 1,2-benzisothiazole derivatives represented by formula I

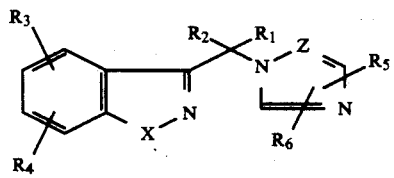

wherein X represents oxygen or sulfur; Z represents carbon (CH) so as to complete the imidazol-1-yl ring radical or Z represents nitrogen (N) so as to complete the 1,2,4-triazol-1-yl ring radical; $R_1$ represents hydrogen lower alkenyl, lower alkynyl, aryl-lower alkyl or lower alkyl; $R_2$ represents hydrogen, lower alkenyl, lower alkynyl, aryl-lower alkyl or lower alkyl; or $R_1$ and $R_2$ combined represent lower alkylene; or $R_1$ combined with $R_5$ located on the Z-carbon atom of the imidazolyl radical represents $C_2$–$C_4$-alkylene; $R_3$ and $R_4$ independently represent hydrogen, lower alkyl, cycloalkyl, halogen, trifluoromethyl, cyano, nitro, amino, hydroxy, lower alkanoyloxy, carbocyclic aroyloxy, lower alkoxy, or carbocyclic aryl; or $R_3$ and $R_4$, together when located on adjacent carbon atoms, represent lower alkylenedioxy; or $R_3$ and $R_4$, together when located on adjacent carbon atoms, represent 1,3-butadienylene or $C_3$–$C_5$-alkylene to form with the carbon atoms to which such is attached a benzo-fused or $C_5$–$C_7$-cycloalka-fused ring, respectively; $R_5$ located on carbon represents hydrogen, lower alkyl or hydroxy-lower alkyl; $R_6$ located on carbon represents hydrogen or lower alkyl; or when Z represents carbon, $R_5$ located on the Z-carbon atom combined with $R_6$ located on the adjacent carbon atom represents $C_3$–$C_5$-alkylene; and pharmaceutically acceptable salts thereof; which are useful in mammals as anticonvulsant agents.

The instant invention is further concerned with processes for preparing said compounds, with pharmaceutical compositions comprising said compounds, and with a method of treating convulsive conditions and diseases in mammals by administration of said compounds or of pharmaceutical compositions comprising said compounds.

The compounds of the invention are of particular interest as broad spectrum anticonvulsant agents in mammals. The compounds of the invention are therefore useful when administered alone or in combination for the treatment of convulsive disorders, particularly epilepsy comprising grand mal, petit mal and status epilepticus types, in mammals, including man.

DETAILED DESCRIPTION OF THE INVENTION

Particular embodiments of the invention relate to the compounds of formula I and pharmaceutically acceptable salts thereof (a) wherein X represents oxygen and Z represents carbon;
(b) wherein X represents oxygen and Z represents nitrogen;
(c) wherein X represents sulfur and Z represents carbon; and
(d) wherein X represents sulfur and Z represents nitrogen.

Further embodiments of the invention relate to compounds of formula I and pharmaceutically acceptable salts thereof wherein in turn (a) $R_1$ and $R_2$ independently represent hydrogen, lower alkenyl, lower alkynyl, aryl-lower alkyl or lower alkyl or together represent lower alkylene; and
(b) when Z represents carbon, $R_1$ together with the substituent on said carbon at the 5-position of the imidazolyl radical represents $C_2$–$C_4$ alkylene, and $R_2$ represents hydrogen or lower alkyl.

Further embodiments also relate to said compounds of formula I and pharmaceutically acceptable salts thereof wherein in turn (a) $R_3$ and $R_4$ independently represent hydrogen, lower alkyl, cycloalkyl, halogen, trifluoromethyl, cyano, nitro, amino, hydroxy, lower alkanoyloxy, carbocyclic aroyloxy, lower alkoxy, or carbocyclic aryl; or $R_3$ and $R_4$, when located on adjacent carbon atoms, together represent lower alkylenedioxy;
b) $R_3$ and $R_4$ together when located on adjacent carbon atoms represent 1,3-butadienylene to form a benzo-fused ring;
(c) $R_3$ and $R_4$ together when located on adjacent carbon atoms represent $C_3$–$C_5$-alkylene to form a corresponding cycloalka-fused ring.

A specific embodiment of the invention relates to the compounds of formula I and pharmaceutically acceptable salts thereof wherein X represents oxygen and Z represents carbon (CH), i.e. the imidazolylmethyl-substituted 1,2-benzisoxazole derivatives of formula IIa

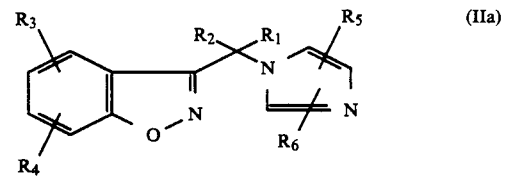

wherein $R_1$ and $R_2$ independently represent hydrogen, aryl-lower alkyl, lower alkenyl, lower alkynyl or lower alkyl; or $R_1$ and $R_2$ together represent lower alkylene; $R_3$ and $R_4$ independently represent hydrogen, lower alkyl, cycloalkyl, halogen, trifluoromethyl, cyano, nitro, amino, hydroxy, lower alkanoyloxy, carbocyclic aroyloxy, lower alkoxy, or carbocyclic aryl; or $R_3$ and $R_4$, together when located on adjacent carbon atoms, represent lower alkylenedioxy; $R_5$ and $R_6$ independently represent hydrogen or lower alkyl; and pharmaceutically acceptable salts thereof.

Preferred are said compounds of formula IIa wherein $R_1$ represents hydrogen or lower alkyl; $R_2$ represents hydrogen or lower alkyl; $R_3$ represents hydrogen, lower alkyl, $C_5$–$C_7$-cycloalkyl, halogen, trifluoromethyl, cyano, nitro, amino, hydroxy, lower alkanoyloxy, carbocyclic aroyloxy, lower alkoxy or carbocyclic aryl; $R_4$ represents hydrogen, lower alkyl, lower alkoxy or halogen; or $R_3$ and $R_4$ together when located on adjacent carbon atoms represent lower alkylenedioxy; $R_5$ and $R_6$ represent hydrogen or lower alkyl; and pharmaceutically acceptable salts thereof.

Further preferred are compounds of formula IIa wherein $R_1$ represents hydrogen or lower alkyl; $R_2$ represents hydrogen or lower alkyl; $R_3$ represents hydrogen, halogen, trifluoromethyl, lower alkyl or phenyl; $R_4$ represents hydrogen, halogen or lower alkyl; $R_5$ is located at the 4-position of the imidazolyl ring and represents hydrogen or lower alkyl; $R_6$ is located at the 5-position of the imidazolyl ring and represents hydrogen or lower alkyl; and pharmaceutically acceptable salts thereof.

Particularly preferred are said compounds of formula IIa wherein $R_1$ represents hydrogen or lower alkyl; $R_2$ represents hydrogen; $R_3$ represents hydrogen, lower alkyl, trifluoromethyl, halogen or phenyl; $R_4$, $R_5$ and $R_6$ represent hydrogen; and pharmaceutically acceptable salts thereof.

A further specific embodiment relates to the triazolylmethyl-substituted 1,2-benzisoxazole derivatives of formula IIb

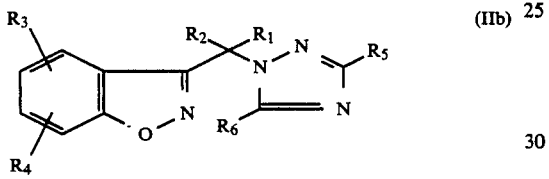

wherein $R_1$ and $R_2$ independently represent hydrogen, aryl-lower alkyl, lower alkenyl, lower alkynyl or lower alkyl; or $R_1$ and $R_2$ together represent lower alkylene; $R_3$ and $R_4$ independently represent hydrogen, lower alkyl, cycloalkyl, halogen, trifluoromethyl, cyano, nitro, amino, hydroxy, lower alkanoyloxy, carbocyclic aroyloxy, lower alkoxy, or carbocyclic aryl; or $R_3$ and $R_4$, together when located on adjacent carbon atoms, represent lower alkylenedioxy; $R_5$ and $R_6$ represent hydrogen or lower alkyl; and pharmaceutically acceptable salts thereof.

Preferred are said compounds of formula IIb wherein $R_1$ represents hydrogen or lower alkyl; $R_2$ represents hydrogen or lower alkyl; $R_3$ represents hydrogen, lower alkyl, $C_5$–$C_7$-cycloalkyl, halogen, trifluoromethyl, cyano, nitro, amino, hydroxy, lower alkanoyloxy, carbocyclic aroyloxy, lower alkoxy or carbocyclic aryl; $R_4$ represents hydrogen, lower alkyl, lower alkoxy or halogen; or $R_3$ and $R_4$ together when located on adjacent carbon atoms represent lower alkylenedioxy; or $R_3$ and $R_4$ together with the adjacent carbon atoms to which they are attached represent fused benzo or fused $C_5$–$C_7$-cycloalka; $R_5$ and $R_6$ represent hydrogen or lower alkyl; and pharmaceutically acceptable salts thereof.

Further preferred are compounds of formula IIb wherein $R_1$ represents hydrogen or lower alkyl; $R_2$ represents hydrogen or lower alkyl; $R_3$ represents hydrogen, halogen, trifluoromethyl, lower alkyl or phenyl; $R_4$ represents hydrogen, halogen or lower alkyl; $R_5$ and $R_6$ represent hydrogen or lower alkyl; and pharmaceutically acceptable salts thereof.

Particularly preferred are said compounds of formula IIb wherein $R_1$ represents hydrogen or lower alkyl; $R_2$ represents hydrogen; $R_3$ represents hydrogen, lower alkyl, trifluoromethyl, halogen or phenyl; $R_4$, $R_5$ and $R_6$ represent hydrogen; and pharmaceutically acceptable salts thereof Preferred embodiments of the invention also pertain to the 1,2-benzisothiazole derivatives corresponding to the above-cited 1,2-benzisoxazole derivatives of formulae IIa and IIb (O being replaced by S in the bicyclic ring grouping).

Another particular embodiment of the invention relates to the naphth[2,3-d]-(isoxazole and isothiazole) derivatives of formula IIIa and naphth[2,1-d]-(isoxazole and isothiazole) derivatives of formula IIIb.

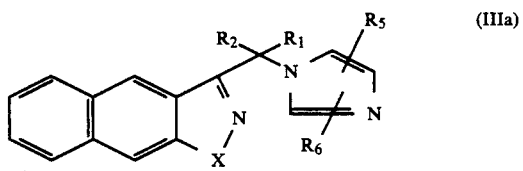

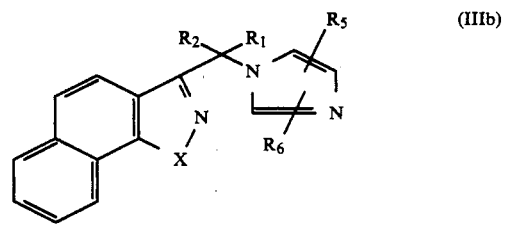

where X represents oxygen or sulfur; $R_1$, $R_2$, $R_5$ and $R_6$ independently represent hydrogen or lower alkyl; and pharmaceutically acceptable salts thereof Preferred are said compounds of formula IIIa and IIIb wherein X represents oxygen.

Another particular embodiment of the invention relates to the compound of the formula IIIc

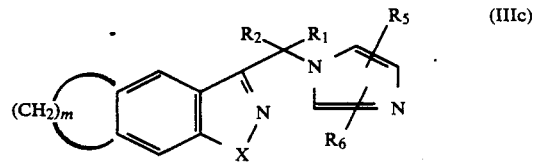

wherein X represents oxygen or sulfur; m represents the integer 3, 4 or 5, particularly 3 or 4; $R_1$, $R_2$, $R_5$ and $R_6$ independently represent hydrogen or lower alkyl; and pharmaceutically acceptable salts thereof.

Preferred are said compounds of formula IIIc wherein X represents oxygen. Further preferred are the compounds wherein m represents the integer 3 or 4, respectively.

Further embodiments relate to the 1,2,4-triazol-1-yl derivatives corresponding to the imidazolyl derivatives of formula IIIa, IIIb and IIIc.

An additional particular embodiment of the invention relates to the compounds of formula IV

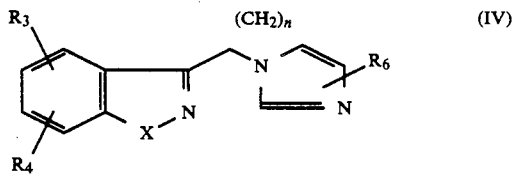

wherein n represents the integer 2, 3 or 4; X represents oxygen or sulfur; $R_3$ represents hydrogen, halogen, trifluoromethyl, lower alkyl or phenyl; $R_4$ represents hydrogen, halogen or lower alkyl; $R_6$ represents hydrogen or lower alkyl; and pharmaceutically acceptable salts thereof.

Further preferred are said compounds of formula IV wherein $R_3$ represents hydrogen, lower alkyl, halogen, trifluoromethyl or phenyl; $R_4$ and $R_6$ represent hydrogen; and pharmaceutically acceptable salts thereof Particularly preferred are said compounds of formula IV wherein n represents the integer 2 or 3; and pharmaceutically acceptable salts thereof.

Most preferred are the said compounds of formula IV wherein X represents oxygen; and pharmaceutically acceptable salts thereof.

Most particularly preferred are said compounds of formula IV wherein X represents oxygen; n represents the integer 3; $R_3$ represents hydrogen, lower alkyl, halogen, trifluoromethyl or phenyl; $R_4$ and $R_6$ represent hydrogen; and pharmaceutically acceptable salts thereof.

The general definitions used herein have the following meaning in the context of the invention.

The term "lower", when referred to above and hereinafter in connection with organic groups, radicals or compounds respectively, defines such with 1 up to and including 7, preferably 1 up to and including 4 and advantageously one, two or three carbon atoms.

A lower alkyl group is either straight chain or branched, preferably contains 1-4 carbon atoms, and represents for example ethyl, propyl, isopropyl, butyl, isobutyl, or advantageously methyl.

A lower alkenyl group preferably contains 3 to 7 carbon atoms and represents for example allyl.

A lower alkynyl group preferably contains 3 to 7 carbon atoms and represents for example propargyl.

A lower alkylene linking group preferably contains 1-4 carbon atoms and represents for example methylene, ethylene, propylene, i.e. 1,2- or 1,3-propylene, butylene, i.e. 1,2-, 1,3- or 1,4-butylene.

A lower alkylenedioxy group represents preferably methylenedioxy or ethylenedioxy.

A lower alkoxy group preferably contains 1-4 carbon atoms and represents for example, ethoxy, propoxy or advantageously methoxy.

Lower alkanoyl as in lower alkanoyloxy preferably contains 2-7 carbon atoms and represents advantageously acetyl, propionyl, n-butyryl, isobutyryl or pivaloyl.

Lower alkanoyloxy represents advantageously acetoxy, propionyloxy, n- or i- butyryloxy or pivaloyloxy (trimethylacetyloxy).

Halogen is preferably fluoro, bromo and chloro, but may also represent iodo.

Carbocyclic aroyl represents carbocyclic arylcarbonyl, preferably benzoyl or benzoyl substituted by one to three substituents selected from lower alkyl, lower alkoxy, trifluoromethyl and halogen; or 1- or 2-naphthoyl.

Carbocyclic aroyloxy represents preferably benzoyloxy, benzoyloxy substituted on the phenyl ring by trifluoromethyl, lower alkyl, halogen or lower alkoxy, e.g. methyl, chloro or methoxy respectively; or 1- or 2-naphthoyl.

Aryl represents preferably carbocyclic aryl.

Aryl-lower alkyl preferably represents carbocyclic aryl-$C_1$-$C_4$-alkyl, advantageously benzyl.

Carbocyclic aryl represents preferably optionally substituted phenyl, e.g. phenyl or phenyl substituted by one to three substituents selected from lower alkyl, lower alkoxy, trifluoromethyl and halogen; or 1- or 2-naphthyl.

Cycloalkyl represents preferably $C_5$-$C_7$-cycloalkyl such being cyclopentyl, cyclohexyl and cycloheptyl, advantageously cyclohexyl.

Pharmaceutically acceptable salts are preferably acid addition salts of preferably pharmaceutically acceptable inorganic or organic acids, such as of strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, ascorbic, maleic, fumaric, pyruvic, pamoic, nicotinic, methanesulfonic, ethanesulfonic, hydroxyethanesulfonic, benzenesulfonic, p-toluenesulfonic or naphthalenesulfonic acid.

The compounds of the invention exhibit valuable pharmacological properties, particularly anticonvulsant properties. The compounds are thus useful for treating convulsive disorders (epilepsy) in mammals.

These effects are demonstrable particularly in in vivo animal tests using advantageously mammals, e.g. mice, rats, or monkeys. Said compounds can be administered to them enterally or parenterally, advantageously orally or transdermally, or subcutaneously, intravenously or intraperitoneally, for example, within gelatin capsules, or in the form of aqueous suspensions or solutions, respectively. The applied in vivo dosage may range between about 0.1 to 100 mg/kg, preferably between about 1.0 and 50 mg/kg, advantageously between about 5 to 30 mg/kg.

The anticonvulsant activity of the compounds of the invention is determined in standard anticonvulsant assay methods, e.g. in the maximal electroshock test and the pentylenetetrazole (PTZ, Metrazol) seizure test in the rat; see J. Pharmacol. Exp. Ther. 235, 98 (1985). The $ED_{50}$, representing the dose of compound required to protect 50% of the animals against electroshock induced convulsions or metrazole-induced convulsions, is determined.

Illustrative of the invention 5-chloro-3-[1-(1H-imidazol-1-yl)ethyl]-1,2-benzisoxazole hydrochloride has an ED50 of about 5 mg/kg p.o. for preventing seizures produced by maximal electroshock in the rat. Furthermore, said compound also blocks pentylenetetrazole induced seizures in the rat with an $ED_{50}$ of about 10 mg/kg p.o.

The aforementioned properties, indicative of broad spectrum anticonvulsant activity, render the compounds of the invention useful for the treatment of epilepsy in mammals, including man.

The compounds of the invention are prepared by the following methods:

(a) Compounds of the invention, i.e. the compounds of formula I and derivatives thereof cited hereinabove are generally prepared by condensing a compound of the formula

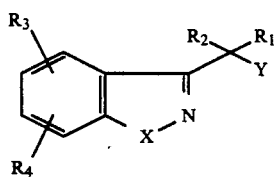

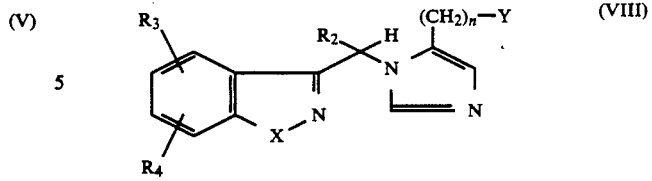

wherein R₁–R₄ and X have meaning as defined above; and Y represents a reactive esterified hydroxy group; with a compound of the formula VIa or VIb

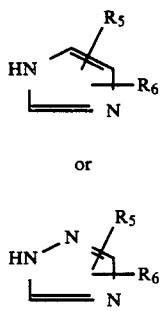

wherein $R_5$ represents hydrogen, lower alkyl or hydroxy-lower alkyl (advantageously in protected form) and $R_6$ represents hydrogen or lower alkyl; and, if required, converting a resulting compound into another compound of the invention.

(b) The compounds of the invention represented by formula I wherein Z represents carbon and derivatives thereof can also be prepared by condensing a compound of formula V as defined above with a compound of the formula VII

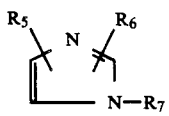

wherein $R_5$ represents hydrogen, lower alkyl or hydroxy-lower alkyl; $R_6$ represents hydrogen or lower alkyl; $R_7$ represents a protecting group; subsequently hydrolyzing, advantageously in situ, the resulting N-substituted quaternary salt to obtain a compound of the formula I or derivative thereof wherein the ring atom at Z represents carbon.

A protecting group $R_7$ for the imidazolyl nitrogen is preferably tri-lower alkylsilyl, e.g. trimethylsilyl, lower alkanoyl e.g. acetyl, di-lower alkylcarbamoyl such as dimethylcarbamoyl, or triarylmethyl e.g. triphenylmethyl.

(c) The compounds of the invention of formula I wherein Z represents carbon and $R_1$ together with the substituent $R_5$ on the Z carbon atom of the imidazolyl radical represents lower alkylene, as illustrated by the compounds of formula IV hereinabove, are prepared by cyclizing, e.g. a compound of the formula VIII wherein X, $R_2$, $R_3$ and $R_4$ have meaning as defined above and Y represents reactive esterified hydroxy, in the presence of a base.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into the free compound or into another salt; and/or a mixture of isomers or racemates obtained is separated into the single isomers or racemates; and/or, if desired, a racemate is resolved into the optical antipodes.

A reactive esterified hydroxy group as mentioned herein represents a leaving group, particularly hydroxy esterified by a strong acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. Said reactive esterified hydroxy group is especially halo, for example chloro, bromo or iodo, or aliphatically or aromatically substituted sulfonyloxy, for example methanesulfonyloxy, phenylsulfonyloxy or 4-methylphenylsulfonyloxy (tosyloxy).

In starting compounds and intermediates therefor which are converted to the compounds of the invention in a manner described herein, functional groups present, such as carboxy, amino (including ring NH) and hydroxy groups, are optionally protected by conventional protecting groups that are common in preparative organic chemistry. Protected carboxy, amino and hydroxy groups are those that can be converted under mild conditions into free carboxy, amino and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy group, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1984.

The condensation according to process (a) can be carried out according to N-alkylation procedures well-known in the art, either as such or in the presence of a base such as triethylamine or pyridine in an inert solvent, e.g. acetonitrile or dichloromethane, at room temperature or near the boiling point of the solvent used.

The condensation is advantageously carried out in the presence of a strong base such as an alkali metal hydride (e.g. sodium or potassium hydride), an alkoxide butoxide) or an amide (e.g. lithium diisopropylamide), or a lower alkyl lithium (e.g. butyl lithium using an inert solvent such as dimethylformamide or tetrahydrofuran.

Process (a) is advantageously used for the preparation of compounds wherein $R_1$ and $R_2$ represent hydrogen, and additional substituents $R_1$ and/or $R_2$ are subsequently introduced as described herein if required.

The imidazole and triazole starting materials of formulae VIa and VIb are either known or are prepared according to methods known in the art and illustrated in the examples.

The starting materials of formula V are also either known or prepared according to methods known in the art, as described e.g. in Chimie Therapeutique 1972, 127-132 Phytochemistry, 1971, 539, J. Heterocyclic Chem. 8, 397 (1971) and Chem. Pharm. Bull. 24, 632-643 (1976) for 1,2-benzisoxazole derivatives and e.g. in Chem. Pharm. Bull. 26, 3888 (1978) for 1,2-benzisothiazole derivatives, e.g. from the corresponding 4-hydroxycoumarins or 4-hydroxythiocoumarins.

The condensation according to process (b) is carried out according to N-alkylation procedures well-known in the art for preparing quaternary salts, in an inert solvent such as acetonitrile or dichloromethane, at room temperature or near the boiling of the solvent used.

Alkylation in this process occurs on the second unprotected imidazole nitrogen to first form a quaternary compound which is advantageously deprotected in situ by hydrolysis with acid or base prior to the isolation of the resulting product of formula I, e.g. with ammonia when the protecting group is di-lower alkylcarbamoyl.

The cyclization according to process (c) is carried out with a strong base, such as an alkali metal hydride (e.g. sodium or potassium hydride), an alkali metal alkoxide (e.g. potassium t-butoxide), an alkali metal amide (e.g. lithium diisopropylamide, or a lower alkyl lithium (e.g. butyl lithium) in an inert solvent such as dimethylformamide or tetrahydrofuran.

The starting materials of formula VIII are prepared by halogenating the alcohols (Y=OH) corresponding to the compounds of formula VIII, e.g. by treatment with thionyl chloride to obtain compounds of formula VIII wherein Y represents chloro. Said alcohols (being compounds of formula I wherein $R_5$ represents hydroxyalkyl) are prepared advantageously by process (b) given above. The appropriate 4-hydroxyalkylimidazole, in which the hydroxy group is protected e.g. in the form of a trialkylsilyl derivative, is preferably first acylated on the imidazole nitrogen at the 1-position with e.g. dimethylcarbamoyl chloride and subsequently alkylated with the appropriate intermediate of formula V.

Furthermore, compounds of formula I can be converted to other compounds of the invention using methods well-known in the art.

For example, a compound of formula I wherein $R_1$ and $R_2$ represent hydrogen can be converted to a compound of formula I wherein one of $R_1$ and $R_2$ represents lower alkyl by alkylating a compound with a reactive esterified derivative of a lower alkanol, e.g. a lower alkyl halide using a strong base, such as an alkali metal hydride (e.g. sodium or potassium hydride), an alkali metal alkoxide (e.g. potassium t-butoxide), an alkali metal amide (e.g. lithium diisopropylamide, or a lower alkyl lithium (e.g. butyl lithium) in an inert solvent such as dimethyl formamide or tetrahydrofuran.

Similarly a compound of formula I wherein one of $R_1$ and $R_2$ represents lower alkyl can be converted to a compound of formula I wherein both $R_1$ and $R_2$ represent lower alkyl.

The above procedures are also similarly used for introducing $R_1$ and/or $R_2$ representing aryl-lower alkyl, lower alkenyl or lower alkynyl.

A compound of formula I wherein $R_1$ and $R_2$ represent hydrogen can also be converted to a compound of formula I wherein one of $R_1$ and $R_2$ represents lower alkyl, by treating said compound with a corresponding lower alkylcarboxaldehyde in the presence of a strong base as cited above, subsequently dehydrating the resulting alcohol, and reducing the double bond in the resulting lower alkylidenyl derivative according to methods well-known in the art.

A compound of formula I wherein $R_1$ and $R_2$ represent hydrogen can also be converted to a compound of formula I wherein $R_1$ and $R_2$ combined represent lower alkylene by treatment with a reactive esterified derivative of a corresponding lower alkylenediol, e.g. of a terminal alkylenediol, either in one step or in sequential fashion using two mole equivalents of a strong base such as an alkali metal hydride (e.g. sodium or potassium hydride), an alkali metal alkoxide (e.g. potassium t-butoxide), an alkali metal amide (e.g. lithium diisopropylamide), or a lower alkyl lithium (e.g. butyl lithium) in an inert solvent such as dimethylformamide or tetrahydrofuran.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures preferably at the boiling point of the solvents used, and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Mainly those starting materials should be used in said reactions, that lead to the formation of those compounds indicated above as being especially preferred.

The invention also relates to any novel starting materials and processes for their manufacture.

Depending on the choice of starting materials and methods, the new compounds may be in the form of one of the possible isomers or mixtures thereof, for example, depending on the number of asymmetrical carbon atoms, as pure optical isomers, such as antipodes, or as mixtures of optical isomers such as racemates or as mixtures of diastereoisomers. The aforesaid possible isomers or mixtures thereof are within the purview of this invention.

Any resulting mixtures of diastereoisomers, mixtures of racemates can be separated on the basis of the physico-chemical differences of the constituents, in known manner, into the pure optical isomers, diastereoisomers, racemates, for example by chromatography and/or fractional crystallization.

Any resulting racemates can be resolved into the optical antipodes by known methods, e.g. by separation of the diastereisomeric salts thereof, with an optically active acid, and liberating the optically active basic compound by treatment with a standard base. Racemic products of the invention can thus be resolved into their optical antipodes, e.g., by the fractional crystallization of d- or l-(tartrate, mandelate or camphorsulfonate) salts. Advantageously, the more active of the two antipodes is isolated.

Finally the compounds of the invention are either obtained in the free form, or as a salt thereof Any resulting base can be converted into a corresponding acid addition salt, preferably with the use of a therapeutically useful acid or anion exchange preparation, or a resulting salt can be converted into the corresponding free base, for example, with the use of a stronger base, such as a metal or ammonium hydroxide or a basic salt, e.g. an alkali metal hydroxide or carbonate, or a cation exchange preparation, or an alkylene oxide such as propylene oxide. These or other salts, for example, the picrates, can also be used for purification of the bases obtained; the bases are converted into salts, the salts are separated and the bases are liberated from the salts.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal and parenteral administration to mammals, including man, for the treatment of convulsive disorders (epilepsy) comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders e.g. magnesium aluminum silicate, starch paste, gelatin, tragacanth, methylcellulose, sodium carboxymethylcellulose and/or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The invention also relates to a method of treatment of convulsive disorders (epilepsy) in mammals, using an effective amount of a compound of the invention as a pharmacologically active substance, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 10 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between abut 15 and 100 mm Hg. The structure of final products, intermediates and starting materials is confirmed by standard analytical methods, e.g. microanalysis and spectroscopic characteristics (e.g. MS, IR, NMR).

EXAMPLE 1

(a) Sodium hydride (60% in mineral oil, 276.6 g, 6.92 moles) is added in portions to a solution of imidazole (471 g, 6.92 moles) in dimethylformamide (4 L) over a period of 1 hour. After the addition is complete, the resulting suspension is stirred for 1 hour at ambient temperature. A solution of 5-chloro-3-bromomethyl-1,2-benzisoxazole (1.57 kg, 6.37 moles) in dimethylformamide (3 L) is then added over a period of 30 minutes, during which time there is an exotherm from 24° C. to 68° C. On completion of this addition, the reaction mixture is stirred and heated at 90° C. for 2 hours. The solvent is then removed in vacuo and the residue is taken up in methylene chloride (4 L). The resulting suspension is washed with water (2×2 L), which dissolves the solid material, and the organic solution is then dried over anhydrous sodium sulfate (1 kg), filtered and evaporated to give 5-chloro-3-[(1H-imidazol-1-yl)methyl]-1,2-benzisoxazole, m.p. 100–102° C.; hydrochloride salt, m.p. 201–203° C.

The starting material is obtained as follows:

A suspension of alpha-bromo-5-chloro-1,2-benzisoxazole-3-acetic acid (3.39 Kg, 11.7 moles) in toluene (12 L) is heated at 96° C. for 18 hours. The solution is cooled room temperature and washed with water (2×4 L), saturated sodium bicarbonate solution (2×4 L) and water (2×4 L) before drying over anhydrous sodium sulfate (1 Kg) and filtering. The filtrate is evaporated in vacuo to afford the crude 5-chloro-3-bromomethyl-1,2-benzisoxazole, m.p. 83–85° C.

Alpha-bromo-5-chloro-1,2-benzisoxazole-3-acetic acid is obtained from 5-chloro-1,2-benzisoxazole-3-acetic acid according to e.g. Chimie Therapeutique 1972, 127.

(b) Sodium hydride (50% in mineral oil, 3.4 g, 0.071 mole) is washed free of mineral oil with hexane (3×30 mL) and suspended in dimethylformamide (100 mL). This suspension is well stirred and maintained near room temperature (water bath) during the dropwise addition of a solution of imidazole (4.8 g, 0.071 mole) in dimethylformamide (25 mL). The reaction mixture is stirred at room temperature for 1 hour when 3-bromomethyl-1,2-benzisoxazole (15.0 g, 0.071 mole) is added all at once. The mixture is then heated at 85° C. for 8 hours. The solvent is evaporated in vacuo and the residue is taken up in methylene chloride (200 mL) and washed with water (3×50 mL). The organic solution is dried over anhydrous sodium sulfate, filtered and evaporated to give 3-[(1H-imidazol-1-yl)methyl]-1,2-benzisoxazole, which is purified by recrystallisation from isopropanol, m.p. 52–55° C. The free base is converted to the hydrochloride salt m.p. 145–146° C., when its solution in isopropanol is treated with a small excess of ethereal hydrogen chloride.

The known 3-bromomethyl-1,2-benzisoxazole (Chem. Pharm. Bull. 24, 632 (1972)) starting material is prepared as follows:

Alpha-bromo-1,2-benzisoxazole-3-acetic acid (58.0 g, 0.23 mole) is suspended in toluene (350 mL) and the mixture is stirred at reflux for 18 hours. The solvent is evaporated and the residue is taken up in methylene chloride (250 mL). This solution is washed with saturated aqueous sodium bicarbonate (2×50 mL), water (50 mL) and dried over anhydrous magnesium sulfate. The solution is filtered and evaporated to afford 3-bromomethyl-1,2-benzisoxazole, m.p. 60–62° C. The compound is purified by recrystallisation from ether-hexane, m.p. 64–66° C.

(c) Similarly condensation of 3-bromomethyl-1,2-benzisoxazole with 1,2,4-triazole affords 3-[(1H-1,2,4-triazol-1-yl)methyl]-1,2-benzisoxazole, m.p. 102–104° C.

The following compounds are also similarly prepared from appropriate starting materials:

(d) 3-[(2-methyl-1H-imidazol-1-yl)methyl]-1,2-benzisoxazole, m.p. 84–86° C.

(e) 3-[4-methyl-1H-imidazol-1-yl)methyl]-1,2-benzisoxazole hydrochloride, m.p. 225–227° C.

(f) 5-bromo-3-[(1H-imidazol-1-yl)methyl]-1,2-benzisoxazole hydrochloride, m.p. 230–232° C.

(g) 5-bromo-3-[(1H-1,2,4-triazol-1-yl)methyl]-1,2-benzisoxazole hydrochloride, m.p. 187–189° C.

(h) 5-bromo-3-[(4-methyl-1H-imidazol-1-yl)-(methyl]-1,2-benzisoxazole hydrochloride, m.p. 188–190° C.

(i) 5-chloro-3-[(1H-1,2,4-triazol-1-yl)methyl]-1,2-benzisoxazole hydrochloride, m.p. 173–175° C.

(j) 5-methyl-3-[(1H-imidazol-1-yl)methyl]-1,2-benzisoxazole hydrochloride, m.p. 178–180° C; starting material: 5-methyl-3-bromomethyl-1,2-benzisoxazole, NMR (CH₂ methylene): 5.35 (s) ppm.

(k) 5-methyl-3-[(1H-1,2,4-triazol-1-yl)methyl]-1,2-benzisoxazole hydrochloride, m.p. 172–174° C.

(l) 5-fluoro-3-[(1H-imidazol-1-yl)methyl]-1,2-benzisoxazole hydrochloride, m.p. 179–181° C; starting material:

(m) 5-fluoro-3-bromomethyl-1,2-benzisoxazole, m.p. 48–50° C.

(m) 5-fluoro-3-[1H-1,2,4-triazol-1-yl)methyl]-1,2-benzisoxazole hydrochloride, m.p. 160–162° C. n) 6-chloro-3-[(1H-imidazol-1-yl)methyl]-1,2-benzisoxazole hydrochloride, m.p. 224–226° C; starting material: -chloro-3-bromomethyl-1,2-benzisoxazole, m.p. 80–82° C.

(o) 6-chloro-3-[(1H-1,2,4-triazol-1-yl)methyl]-1,2-benzisoxazole hydrochloride, m.p. 175–177° C.

(p) 6-chloro-3-[(4-methyl-1H-imidazol-1-yl)methyl]-1,2-benzisoxazole hydrochloride, m.p. 185–187°C.

(q) 5-phenyl-3-[(1H-imidazol-1-yl)methyl]-1,2-benzisohydrochloride, m.p. 198–200° C; starting material: 5-phenyl-3-bromomethyl-1,2-benzisoxazole, m.p. 87–90° C.

(r) 5,6-dimethyl-3-[(1H-imidazol-1-yl)methyl]-1,2-benzisoxazole hydrochloride, m.p. 223–224° C; starting material: 5,6-dimethyl-3-bromomethyl-1,2-benzisoxazole, m.p. 41–44° C, prepared from 6,7-dimethyl-4-hydroxycoumarin, J. Med. Chem. 18, 391 (1975).

(s) 5-chloro-3-[(4-methyl-1H-imidazol-1-yl)methyl]-1,2-benzisoxazole hydrochloride, m.p. 228–230° C.

(t) 5-fluoro-3-[(4-methyl-1H-imidazol-1-yl)methyl]-1,2-benzisoxazole hydrochloride, m.p. 240–242° C.

(u) 3-[(4,5-dimethyl-1H-imidazol-1-yl)methyl]-1,2-benzisoxazole hydrochloride, m.p. 197–198° C.

(v) 5-phenyl-3-[(1H-1,2,4-triazol-1-yl)methyl]-1,2-benzisoxazole hydrochloride, m.p. 142–144° C.

Example 2

The following compounds are prepared using procedures similar to those described in Example 1:

(a) 3-[(1H-imidazol-1-yl)methyl]naphth-[2,1-d]isoxazole hydrochloride, m.p. 230–232° C; starting material: 3-bromomethyl-naphth-[2,1-d]isoxazole, m.p. 100–103° C, which is prepared from the corresponding benzofused 4-hydroxycoumarin, J. Het. Chem. 18, 587 (1981).

(b) 3-[(1H-imidazol-1-yl)methyl]naphth-[2,3-d]-isoxazole hydrochloride, m.p. 244–246° C.; starting material 3-bromomethyl-naphth-[2,3-d]isoxazole, m.p. 111–113° C., which is prepared from the corresponding benzofused 4-hydroxycoumarin, Indian J. Chem. 11, 115 (1973).

(c) 6,7-dihydro-3-[(1H-imidazol-1-yl)methyl]-5H-indeno[5,6-d]isoxazole hydrochloride, m.p. 207–208° C; starting material: 3-bromomethyl-6,7-dihydro-5H-indeno[5,6-d]isoxazole, m.p. 69–71° C., which is prepared from the corresponding cyclopenta-fused 4-hydroxycoumarin.

The cyclopenta-fused 4-hydroxycoumarin derivative is prepared as follows:

5-Acetoxyindane (Chemical Abstracts, 77, 126112w) is rearranged to 2-acetyl-5-indanol by a Fries Reaction (cf. R. Martin et al., Monatsh. 81, 111 (1980)). The latter is converted into the corresponding 4-hydroxycoumarin derivative according to Link et al., J. Med. Chem., 14, 167 (1971).

EXAMPLE 3

(a) A solution of n-butyl lithium in hexane (2.1 M, 9.2 mL, 0.019 mole) is added dropwise to a solution of diisopropylamine (2.1 g, 0.021 mole) in anhydrous tetrahydrofuran (40 mL) at −40° C. (dry ice/isopropanol bath). After standing at this temperature for 10 minutes, the cold solution is added dropwise to a stirred, cooled (−60° C.) solution of 3-[(1H-imidazol-1-yl)methyl]-1,2-benzisoxazole (3.7 g, 0.019 mole) in anhydrous tetrahydrofuran (40 mL). The resulting deep red colored reaction mixture is stirred at −60° C. for 30 minutes and then iodomethane (4.1 g, 0.029 mole) is added all at once. The reaction is stirred at −60° C. for 1 hour and then without external cooling for a further 2 hours. Water (100 mL) and ethyl acetate (100 mL) are then added and the organic solution is separated and extracted with 3N hydrochloric acid (2×30 mL). The combined acid extracts are subsequently made basic (pH 8) with 2N sodium hydroxide and the product is extracted into ethyl acetate (2×50 mL). The combined extracts are dried over anhydrous sodium sulfate, filtered and evaporated in vacuo to afford an oil which solidifies on standing. The crude 3-[1-(1H-imidazol-1-yl)ethyl]-1,2-benzisoxazole, the compound of formula IIa wherein $R_1$ is methyl and $R_2$ -$R_6$ are hydrogen, is recrystallised from isopropanol, m.p. 62–64° C. When a warm solution of this material in isopropanol is treated with a small excess of ethereal hydrogen chloride, the hydrochloride salt is obtained, m.p. 163–165° C.

The following compounds are similarly prepared (b) 5-chloro-3-[1-(1H-imidazol-1-yl)ethyl]-1,2-benzisoxazole hydrochloride, m.p. 168–170° C.

(c) 3-[1-(5-methyl-1H-imidazol-1-yl)ethyl]-1,2-benzisoxazole hydrochloride, m.p. 215–217° C.

(d) 3-[1-(1H-1,2,4-triazol-1-yl)ethyl]-1,2-benzisoxazole hydrochloride, m.p. 153–155° C.

(e) 3-[1-(1H-imidazol-1-yl)-1-propyl]-1,2-benzisoxazole hemisuccinate, m.p. 108–110° C.

(f) 3-[1-(1H-imidazol-1-yl)-1-pentyl]-1,2-benzisoxazole oxalate, m.p. 68–70° C.

(g) 3-[1-(1H-imidazol-1-yl)-2-methyl-1-propyl]-1,2-benzisoxazole citrate, m.p. 65–68° C.

(h) 3-[1-(1H-imidazol-1-yl)-1-butyl]-1,2-benzisoxazole, m.p. 69–70° C.

(i) 3-[1-(1H-imidazol-1-yl)-1-but-3-enyl]-1,2-benzisoxazole, m.p. 79–80° C.

(j) 3-[1-(1H-1,2,4-triazol-1-yl)-1-propyl]-1,2-benzisoxazole, m.p. 68–70° C.

(k) 5-chloro-3-[1-(1H-imidazol-1-yl)-1-propyl]-1,2-benzisoxazole maleate, m.p. 123–125° C.

(l) 5-chloro-3-[1-(1H-imidazol-1-yl)-2-methyl-1propyl]-1,2-benzisoxazole benzisoxazole maleate, m.p. 88–90° C.

(m) 3-[2-(1H-imidazol-1-yl)-2-propyl]-1,2-benzisoxazole, hydrochloride, m.p. 211–213° C., by reaction as described under a) using 3-[1-(1H-imidazol-1-yl)ethyl]-1,2-benzisoxazole as starting material.

(n) 3-[1-(1H-imidazol-1-yl)-2-phenylethyl]-1,2-benzisoxazole, m.p. 142–143°.

EXAMPLE 4

A solution of 5-chloro-3-[(1H-imidazol-1-yl)methyl]-1,2-benzisoxazole (500 g, 2.14 moles) in dimethylformamide (3.5 L) is cooled to −35° C. (dry ice/isopropanol bath) and is subsequently added, all at once, to a precooled (−35° C.) solution of potassium t-butoxide (266 g, 2.37 moles) in dimethylformamide (3.5 L). A deep red color develops immediately. The mixture is stirred at 35° C. for 5 minutes and is then cooled to −55° C. over a period of 10 minutes. At this point, iodomethane (433 g, 3.05 moles) is added all at once. There is an exotherm to −22° C. and then the temperature begins to decrease. At −26° C. the reaction mixture decolorizes, solid potassium bromide separates and there is a mild exotherm to −22° C. which is maintained for 5 minutes. The mixture subsequently cools quickly to −55° C. and stirring is continued for 30 minutes at this temperature. The cooling bath is then removed and the reaction temperature is allowed to rise to 0° C. over a period of 1.5 hours. The reaction mixture is then poured into water (35 L) and the mixture is extracted with ethyl acetate (20 L). The layers are separated and the organic solution is washed with water (6×6 L), dried over anhydrous sodium sulphate (5 Kg), filtered, and evaporated in vacuo. The residual oil is digested with petroleum ether (b.p 40–60° C.) (2×2 L) at room temperature, and the solvent is then decanted and discarded. The digestion process is repeated with ether (4×3 L) and the combined ethereal extracts are dried over anhydrous sodium sulfate (500 g) and filtered. The filtrate is acidified with ethereal hydrogen chloride (500 mL, 6 N) and the suspension cake is washed with ether (2×500 mL) and the product is digested in refluxing acetone (2 L) for 1 hour. The suspension is cooled to room temperature and filtered. The filter cake is washed with acetone (2×500 mL) and ether (2×500 mL) and the product is dried for 18 hours at 60° C./9 mm Hg to afford 5-chloro-3-[1-(1H-imidazol-1-yl)ethyl]1,2-benzisoxazole hydrochloride, m.p. 161–166° C., of formula IIa wherein $R_1$ is methyl, $R_3$ is 5-chloro, $R_2$ and $R_4$ -$R_6$ are hydrogen.

The above product is further purified as follows the hydrochloride salt is dissolved in refluxing absolute ethanol (400 mL), the resulting solution is filtered and the filter cake is washed with hot ethanol (50 mL). Acetone (4 L) is then added all at once to the well-stirred hot ethanolic solution. The resulting suspension is stirred overnight at ambient temperature and then filtered. The filter cake is washed with acetone (2×250 mL), air-dried for 3 hours and finally dried for 18 hours at 70° C./1 mm Hg to give pure 5-chloro-3-[1-(1H-imidazol-1-yl)ethyl]-1,2-benzisoxazole hydrochloride, m.p. 168–169° C.

EXAMPLE 5

(a) A solution containing 5-chloro-3-bromomethyl-1,2-benzisoxazole (2.5 g, 0.010 mole) and 1-dimethylcarbamoyl-4-methyl-imidazole (1.84 g, 0.012 mole) in anhydrous acetonitrile (25 mL) is stirred at reflux for 72 hours. The solution is cooled to 5° C. (ice-bath) and ammonia gas is bubbled through the solution for 5 minutes after which the solution is allowed to stand at ambient temperature for 1 hour. The solvent is evaporated and the residue is taken up in methylene chloride (25 mL). This solution is washed with water (2×20 mL), dried over anhydrous sodium sulphate, filtered and evaporated to give 5-chloro-3-[(5-methyl-1H-imidazol-1-yl)-methyl]-1,2-benzisoxazole as an oil. A solution of this product in acetone is treated with a slight excess of ethereal hydrogen chloride to afford the hydrochloride salt, m.p. 245–247° C.

The N-dimethylcarbamoyl substituted imidazole starting material is prepared as follows:

A solution containing 4-methylimidazole (17.0 g, 0.25 mole), N,N-dimethylcarbamoyl chloride (27.0 g, 0.25 mole) and triethylamine (30 g, 0.30 mole) in acetonitrile (125 mL) is stirred at reflux for 20 hours. The reaction mixture is cooled, diluted with ether (1000 mL) and filtered. The filtrate is evaporated and the residue is distilled under reduced pressure to afford 1-dimethylcarbamoyl-4-methyl-imidazole, b.p. 104–106° C./0.35 mm Hg.

(b) A solution containing 1-dimethylcarbamoyl-4-(3-trimethylsilyloxypropyl)-imidazole (6.7 g, 0.025 mole), and 3-bromomethyl-1,2-benzisoxazole (5.3 g, 0.025 mole) in anhydrous acetonitrile (30 mL) is stirred at reflux for 72 hours. The reaction mixture is cooled and mixed with a solution of sodium methoxide (3 g, 0.055 mole) in methanol (30 mL). The resulting solution is stirred at reflux for 26 hours. The solvents are evaporated and the residue is taken up in 1N hydrochloric acid (30 mL). This solution is allowed to stand at ambient temperature for 3 hours and is then made basic (pH 9) by addition of 50% aqueous sodium hydroxide solution. The mixture is extracted with methylene chloride (2×25 mL) and the combined extracts are washed with water (2×20 mL), dried over anhydrous sodium sulfate, filtered, and the solvent is evaporated to give crude 3-[(5-(3-hydroxypropyl)-1H-imidazol-1-yl)-methyl]-1,2-benzisoxazole which is purified by trituration with acetone (15 mL), m.p. 129–131° C. The compound forms a hydrochloride hemihydrate, m.p. 155–157° C. when its solution in isopropanol is treated with ethereal hydrogen chloride.

The starting material is prepared as follows 1-Dimethylcarbamoyl-4-(3-hydroxypropyl)-imidazole, NMR (imidazole protons): 2.15 (s) and 2.95 (s) ppm, is prepared by condensing 4-(3-hydroxypropyl)-imidazole with N,N-dimethylcarbamoyl chloride in a similar fashion as described under (a).

1-Dimethylcarbamoyl-4-(3-hydroxypropyl)-imidazole (19.8 g, 0.10 mole) and triethylamine (15 g, 0.15 mole) are dissolved in acetonitrile (100 mL) and the solution is stirred and cooled in an ice bath during the dropwise addition of chlorotrimethylsilane (11.9 g, 0.11 mole). The reaction is stirred at ice-bath temperature for 1 hour and is subsequently allowed to stand at ambient temperature for 15 hours. The mixture is diluted with ether (500 mL), filtered, and the solvent is evaporated to give 1-dimethylcarbamoyl-4-(3-trimethylsilyloxypropyl)imidazole as an oil; NMR (imidazole protons): 2.2 (s) and 3.05 (s) ppm.

EXAMPLE 6

A suspension of 3-[(5-(3-chloropropyl)-1H-imidazol-1-yl)methyl]-1,2-benzisoxazole hydrochloride (1.9 g, 0.006 mole) in anhydrous tetrahydrofuran (25 mL) is stirred under an atmosphere of nitrogen and cooled in an ice bath during the portionwise addition of solid potassium t-butoxide (1.7 g, 0.015 mole). The reaction mixture is stirred at 0–5° C. for 3 hours and then acidified by addition of glacial acetic acid (0.5 mL). The solvent is evaporated and the residue is taken up in methylene chloride (20 mL) and washed with saturated sodium bicarbonate (10 mL) and water (10 mL). The solution is dried over anhydrous sodium sulfate, filtered and evaporated to give crude 3-(5,6,7,8-tetrahydroimidazo[1,5-s]-pyridin-5-yl)-1,2-benzisoxazole which is converted to the hydrochloride salt, m.p. 250–252° C., when its solution in isopropanol is treated with ethereal hydrogen chloride.

The starting material is prepared as follows.

A solution of thionyl chloride (2.4 g, 0.02 mole) in methylene chloride (15 mL) is added dropwise to a suspension of 3-[(5-(3-hydroxypropyl)-1H-imidazol-1-yl)methyl]-1,2-benzisoxazole (2.6 g, 0.01 chloride (15 mL) which is stirred and cooled in an ice-bath. Upon completion of the addition, the reaction mixture is stirred for 1 hour at 0–5° C. and is then stirred at reflux for 2 hours.

The resulting suspension is filtered to give 3-[(5-(3-chloropropyl)-1H-imidazol-1-yl)methyl]-1,2-hydrochloride, m.p. 180–182° C.

EXAMPLE 7

(a) 5-Chloro-3-[1-(1H-imidazol-1-yl)methyl]-1,2-benzisoxazole (1.4 g, 0.0056 mole) is dissolved in acetone (100 mL) and mixed with a solution of levorotatory (-)-tartaric acid (0.042 g, 0.0028 mole) in acetone (5 mL). After standing overnight at ambient temperature, the solid which separates is collected and recrystallised twice from absolute ethanol to afford the tartrate salt, m.p. 149–151° C. The tartrate salt is converted to the free base with dilute aqueous sodium hydroxide. The isolated dextrorotatory biologically more potent enantiomer of 5-chloro-3-[1-(1H-imidazol-1-yl)ethyl]1,2-benzisoxazole, is converted to the hydrochloride salt, m.p. 169–170° C., with ethereal hydrogen chloride in acetone; $[alpha]^{25}D = +5.56°$ (in methanol).

(b) the levorotatory less potent enantiomer is similarly obtained using dextrorotatory (+)-tartaric acid as the resolving agent, and has the following properties:

Tartrate salt: m.p. 149–151° C.

Hydrochloride salt: m.p. 168–170° C.; $[alpha]_{25}D = -5.82°$ in methanol.

EXAMPLE 8

(a) Sodium hydride (50% in mineral oil, 0.28 g, 0.002 mole) is washed free of mineral oil with hexane (3–5 mL) and then suspended in dimethylformamide (5 mL). Imidazole (0.14 g, 0.002 mole) is added to the stirred suspension at room temperature in portions. The resulting mixture is stirred at ambient temperature for 30 minutes and a solution of 3-bromomethyl-1,2-benzisothiazole (0.44 g, 0.002 mole) in dimethylformamide (5 mL) is added dropwise. The reaction mixture is subsequently heated at 80–85° C. for 20 hours before cooling and evaporating the solvent in vacuo. The residue is taken up in a mixture of water (10 mL) and methylene chloride (10 mL). The organic solution is separated, washed with water (5 mL), dried over anhydrous sodium sulphate and evaporated. The crude oily residue of 3-[(1H-imidazol-1-yl)methyl]-1,2-benzisothiazole is taken up in acetone (10 mL) and treated with ethereal hydrogen chloride to afford 3-[(1H-imidazol-1-yl)methyl]1,2-benzisothiazole hydrochloride, m.p. 224–226° C.

The starting material, 3-bromomethyl-1,2-benzisothiazole, is prepared in the manner described by H. Uno et al, Chem. Pharm. Bull., 26 (12), 3888 (1978).

Similarly prepared from appropriate starting materials are:

(b) 5-chloro-3-[(1H-imidazol-1-yl)methyl]-1,2-benzisothiazole hydrochloride;

(c) 3-[(1H-1,2,4-triazol-1-yl)methyl]-1,2-benzisothiazole hydrochloride, by condensation of 3-bromomethyl-1,2-benzisothiazole with 1,2,4-triazole;

(d) 3-[(2-methyl-1H-imidazol-1-yl)methyl]-1,2-benzisothiazole hydrochloride;

(e) 3-[(4-methyl-1H-imidazol-1-yl)methyl]-1,2-benzisothiazole hydrochloride;

(f) 5-bromo-3-[(1H-imidazol-1-yl)methyl]-1,2-benzisothiazole hydrochloride;

(g) 5-bromo-3-[(1H-1,2,4-triazol-1-yl)methyl]-1,2benzisothiazole hydrochloride;

(h) 5-bromo-3-[(4-methyl-1H-imidazol-1-yl)methyl]-1,2-benzisothiazole hydrochloride;

(i) 5-chloro-3-[(1H-1,2,4-triazol-1-yl)methyl]-1,2-benzisothiazole hydrochloride;

(j) 5-methyl-3-[(1H-imidazol-1-yl)methyl]-1,2-benzisothiazole hydrochloride;

(k) 5-methyl-3-[(1H-1,2,4-triazol-1-yl)methyl-1,2-benzisothiazole hydrochloride;
(l) 5-fluoro-3-(1H-imidazol-1-yl)methyl]-1,2-benzisothiazole hydrochloride;
(m) 5-fluoro-3-[(1H-1,2,4-triazol-1-yl)methyl]-1,2-benzisothiazole hydrochloride;
(n) 6-chloro-3-[(1H-imidazol-1-yl)methyl]-1,2-benzisothiazole hydrochloride;
(o) 6-chloro-3-[(1H-1,2,4-triazol-1-yl)methyl]-1,2-benzisothiazole hydrochloride;
(p) 6-chloro-3-[(4-methyl-1H-imidazol-1-yl)methyl]-1,2-benzisothiazole hydrochloride;
(q) 5-phenyl-3-[(1H-imidazol-1-yl)methyl]-1,2-benzisothiazole hydrochloride.
(r) 5,6-dimethyl-3-[(1H-imidazol-1-yl)methyl]-1,2-benzisothiazole hydrochloride;
(s) 5-chloro-3-[(4-methyl-1H-imidazol-1-yl)methyl]-1,2-benzisothiazole hydrochloride;
(t) 5-fluoro-3-[(4-methyl-1H-imidazol-1-yl)methyl]-1,2-benzisothiazole hydrochloride;
(u) 3-[(4,5-dimethyl-1H-imidazol-1-yl)methyl]-1,2-benzisothiazole hydrochloride;
(v) 5-phenyl-3-[(1H-1,2,4-triazol-1-yl)methyl]-1,2-benzisothiazole hydrochloride.

EXAMPLE 9

The following compounds are prepared using procedures similar to those described in the previous Examples.
(a) 3-[1-(1H-imidazol-1-yl)ethyl]-1,2-benzisothiazole hydrochloride;
(b) 5-chloro-3-[1-(1H-imidazol-1-yl)ethyl]-1,2-benzisothiazole hydrochloride;
(c) 3-[1-(5-methyl-1H-imidazol-1-yl)ethyl]-1,2-benzisothiazole hydrochloride;
(d) 3-[1-(1H-1,2,4-triazol-1-yl)ethyl]-1,2-benzisothiazole hydrochloride;
(e) 3-[1-(1H-imidazol-1-yl)-1-propyl]-1,2-benzisothiazole;
(f) 3-[1-(1H-imidazol-1-yl)-1-pentyl]-1,2-benzisothiazole;
(g) 3-[1-(1H-imidazol-1-yl)-2-methyl-1-propyl]1,2-benzisothiazole;
(h) 3-[1-(1H-imidazol-1-yl)-1-butyl]-1,2-benzisothiazole;
(i) 3-[1-(1H-1,2,4-triazol-1-yl)-1-propyl]-1,2-benzisothiazole;
(j) 3-[2-(1H-imidazol-1-yl)-2-propyl]-1,2-benzisothiazole.
(m) 3-[1-(1H-imidazol-1-yl)-2-phenylethyl]-1,2-benzisothiazole.

EXAMPLE 10

(a) Preparation of 10,000 tablets each containing 10 mg of the active ingredient:

| Formula: | |
|---|---|
| 5-chloro-3-[1-(1H-imidazol-1-yl)-ethyl]-1,2-benzisoxazole hydrochloride | 100.00 g |
| Lactose | 2,400.00 g |
| Corn starch | 125.00 g |
| Polyethylene glycol 6,000 | 150.00 g |
| Magnesium stearate | 40.00 g |
| Purified water | q.s |

PROCEDURE:

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

(b) Preparation of 1,000 capsules each containing 10 mg of the active ingredient:

| Formula: | |
|---|---|
| 5-chloro-3-[1-(1H-imidazol-1-yl)-ethyl]-1,2-benzisoxazole hydrochloride | 10.0 g |
| Lactose | 207.0 g |
| Modified starch | 80.0 g |
| Magnesium stearate | 3.0 g |

PROCEDURE:

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

What is claimed is:

1. A compound of the formula

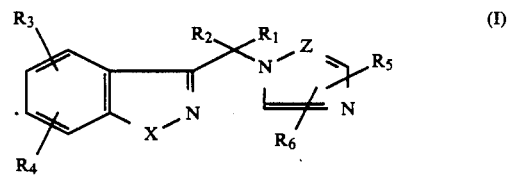

where X represents sulfur, Z represents carbon (CH) so as to complete the imidazol-1yl ring radical or Z represents nitrogen (N) so as to complete the 1,2,4-triazol-1yl ring radical; $R_1$ represents hydrogen, lower alkenyl, lower alkynyl, carbocyclic aryl-lower alkyl or lower alkyl; $R_2$ represents hydrogen, lower alkenyl, lower alkynyl, carbocyclic aryl-lower alkyl or lower alkyl; or $R_1$ and $R_2$ combined represents $C_1$-$C_6$-alkylene; or $R_1$ combined with $R_6$ located on the Z-carbon atom of the imidazolyl radical represents $C_2$-$C_4$ alkylene; $R_3$ and $R_4$ independently represent hydrogen, lower alkyl, $C_5$-$C_7$-cycloalkyl, halogen, trifluoromethyl, cyano, nitro, amino, hydroxy, lower alkanoyloxy, carbocyclic aroyloxy, lower alkoxy or carbocyclic aryl; or $R_3$ and $R_4$, together when located on adjacent carbon atoms, represent lower alkylenedioxy; or $R_3$ and $R_4$, together when located on adjacent carbon atoms, represent 1,3-butadienylene or $C_3$-$C_5$-alkylene to form with the carbon atoms to which such is attached a benzo-fused or $C_5$-$C_7$-cycloalka-fused ring, respectively; $R_5$ located on carbon represents hydrogen, lower alkyl or hydroxy-lower alkyl; $R_6$ located on carbon represents hydrogen or lower alkyl; or when z represents carbon, $R_5$ located on the Z-carbon atom combined with $R_6$ located on the adjacent carbon atom represents $C_3$-$C_5$-alkylene; carbocyclic aryl within the above definitions represents phenyl or phenyl substituted by lower alkyl, lower alkoxy, trifluoromethyl or halogen; carbocyclic aroyloxy represents benzoyloxy, benzoyloxy substituted on the phenyl ring by trifluoromethyl, lower alkyl, halogen or lower alkoxy; or a pharmaceucally acceptable salt thereof.

2. A compound according to claim 1 wherein X represents sulfur and Z represents carbon.

3. A compound according to claim 1 wherein X represents sulfur and Z represents nitrogen.

4. A compound according to claim 2 of the formula

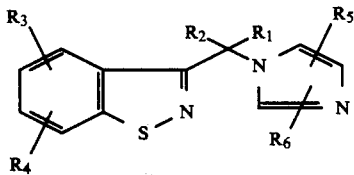

wherein $R_1$ and $R_2$ independently represent hydrogen, lower alkenyl, lower alkynyl, carbocyclic aryl-lower alkyl or lower alkyl; or $R_1$ and $R_2$ together represent lower alkylene; $R_3$ and, $R_4$ independently represent hydrogen, lower alkyl, $C_5$–$C_7$-cycloalkyl, halogen, trifluoromethyl, cyano, nitro, amino, hydroxy, lower alkanoyloxy, carbocyclic aroyloxy, lower alkoxy or carbocyclic aryl; or $R_3$ and $R_4$, together when located on adjacent carbon atoms, represent lower alkylenedioxy; $R_5$ and $R_6$ independently represent hydrogen or lower alkyl; or a pharmaceutically acceptable salt thereof.

5. A compound according to claim 4 wherein $R_1$ represents hydrogen or lower alkyl; $R_2$ represents hydrogen or lower alkyl; $R_3$ represents hydrogen, lower alkyl, $C_5$–$C_7$-cycloalkyl, halogen, trifluoromethyl, cyano, nitro, amino, hydroxy, lower alkanoyloxy, carbocyclic aroyloxy, lower alkoxy or carbocyclic aryl; $R_4$ represents hydrogen, lower alkyl, lower alkoxy or halogen; or $R_3$ and $R_4$ together when located on adjacent carbon atoms represent lower alkylenedioxy; $R_5$ and $R_6$ represent hydrogen or lower alkyl; or a pharmaceutically acceptable salt thereof.

6. A compound according to claim 4 wherein $R_1$ represents hydrogen or lower alkyl; $R_2$ represents hydrogen or lower alkyl; $R_3$ represents hydrogen, halogen, trifluoromethyl, lower alkyl or phenyl; $R_4$ represents hydrogen, halogen or lower alkyl; $R_5$ is located at the 4-position of the imidazolyl ring and represents hydrogen or lower alkyl; $R_6$ is located at the 5-position of the imidazolyl ring and represents hydrogen or lower alkyl; or a pharmaceutically acceptable salt thereof.

7. A compound according to claim 13 wherein $R_1$ represents hydrogen or lower alkyl; $R_2$ represents hydrogen; $R_3$ represents hydrogen, lower alkyl, halogen, trifluoromethyl, or phenyl; $R_4$, $R_5$ and $R_6$ represent hydrogen; or a pharmaceutically acceptable salt thereof 8. A compound according to claim 3 of the formula

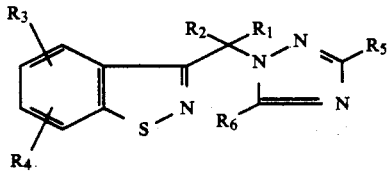

wherein $R_1$ and $R_2$ independently represent hydrogen, lower alkenyl, lower alkynyl, carbocyclic aryl-lower alkyl or lower alkyl; or $R_1$ and $R_2$ together represent lower alkylene; $R_3$ and $R_4$ independently represent hydrogen, lower alkyl, $C_5$–$C_7$-cycloalkyl, halogen, trifluoromethyl, cyano, nitro, amino, hydroxy, lower alkanoyloxy, carbocyclic aroyloxy, lower alkoxy or carbocyclic aryl; or $R_3$ and $R_4$, together when located on adjacent carbon atoms, represent lower alkylenedioxy; $R_5$ and $R_6$ represent hydrogen or lower alkyl; or a pharmaceutically acceptable salt thereof.

9. A compound according to claim 8 wherein $R_1$ represents hydrogen or lower alkyl; $R_2$ represents hydrogen or lower alkyl; $R_3$ represents hydrogen, halogen, trifluoromethyl, lower alkyl or phenyl; $R_4$ represents hydrogen, halogen or lower alkyl; $R_5$ and $R_6$ represent hydrogen or lower alkyl; or a pharmaceutically acceptable salt thereof.

10. A compound according to claim 8 wherein $R_1$ represents hydrogen or lower alkyl; $R_2$ represents hydrogen; $R_3$ represents hydrogen, lower alkyl, trifluoromethyl, halogen or phenyl; $R_4$, $R_5$ and $R_6$ represent hydrogen; or a pharmaceutically acceptable salt thereof 11. A compound according to claim 1 of formula IIIa

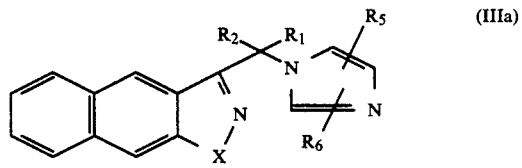

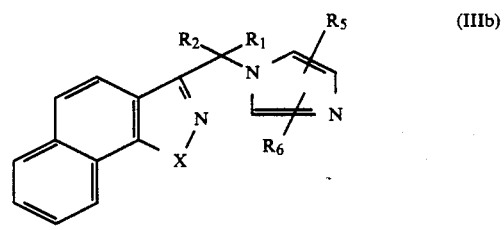

wherein X represents oxygen or sulfur; $R_1$, $R_2$, $R_5$ and $R_6$ independently represent hydrogen or lower alkyl; or a pharmaceutically acceptable salt thereof.

12. A compound according to claim 1 of the formula

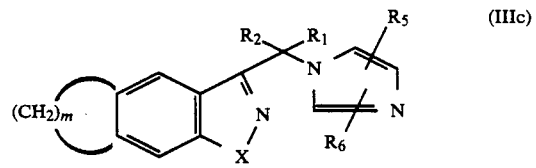

wherein X represent or sulfur; m represents the integer 3, 4 or 5, particularly 3 or 4; $R_1$, $R_2$, $R_5$ and $R_6$ independently represent hydrogen or lower alkyl; or a pharmaceutically acceptable salt thereof.

13. A compound according to claim 1 of the formula

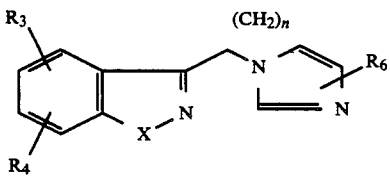

IV wherein n represents the integer 2, 3 or 4; X represents sulfur; $R_3$ represents hydrogen, halogen, trifluoromethyl, lower alkyl or phenyl; $R_4$ represents hydrogen, halogen or lower alkyl; $R_6$ represents hydrogen or lower alkyl; or a pharmaceutically acceptable salt thereof.

14. A pharmaceutical composition for the treatment of convulsions in mammals comprising an anticonvulsant effective amount of a compound of claim 1 in combination with one or more pharmaceutically acceptable carriers.

15. A method of treating epilepsy in mammals comprising the administration to a mammal in need thereof of an anticonvulsant effective amount of a compound of claim 1 or of a pharmaceutical composition comprising a said compound.

16. A compound according to claim 10 being 3-1,2-benzisothiazole or a pharmaceutically acceptable salt thereof.

* * * * *

UNITED STATES PATENT AND TRADEMARK OFFICE
CERTIFICATE OF CORRECTION

PATENT NO. : 4,957,931
DATED : September 18, 1990
INVENTOR(S) : Bowman

It is certified that error appears in the above-identified patent and that said Letters Patent is hereby corrected as shown below:

In column 17, Example 6, line 61 should read:

--yl)-methyl]-1,2-benzisoxazole (2.6 g, 0.01 mole) in methylene chloride (15 --

Signed and Sealed this

Twenty-first Day of July, 1992

*Attest:*

DOUGLAS B. COMER

*Attesting Officer*     *Acting Commissioner of Patents and Trademarks*